US008254652B2

(12) United States Patent
Ma et al.

(10) Patent No.: US 8,254,652 B2
(45) Date of Patent: Aug. 28, 2012

(54) APPARATUS, METHOD AND SYSTEM FOR COMPUTER TOMOGRAPHY IMAGE PROCESSING

(75) Inventors: Hongfeng Ma, Shenyang (CN); Jun Zhang, Shenyang (CN); Songmin Quan, Shenyang (CN); Yan Kang, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 954 days.

(21) Appl. No.: 11/936,879

(22) Filed: Nov. 8, 2007

(65) Prior Publication Data

US 2008/0107230 A1 May 8, 2008

(30) Foreign Application Priority Data

Nov. 8, 2006 (CN) .......................... 2006 1 0138351

(51) Int. Cl.
*G06K 9/00* (2006.01)
(52) U.S. Cl. .............................. 382/131; 600/407; 378/4
(58) Field of Classification Search .................. 382/131; 600/407; 378/4
See application file for complete search history.

(56) References Cited

U.S. PATENT DOCUMENTS

| 6,366,800 | B1 * | 4/2002 | Vining et al. ................. 600/425 |
| 6,396,939 | B1 | 5/2002 | Hu et al. |
| 6,633,627 | B2 * | 10/2003 | Horiuchi ....................... 378/156 |
| 6,658,080 | B1 | 12/2003 | Poole et al. |
| 7,031,423 | B2 * | 4/2006 | Tsukagoshi ....................... 378/4 |

FOREIGN PATENT DOCUMENTS

CN         1395713 A    2/2003

OTHER PUBLICATIONS

Kang et al., "A New Accurate and Precise 3-D Segmentation Method for Skeletal Structures in Volumetric CT Data", 2003, IEEE Trans. on Medical Imaging, vol. 22, No. 5, 586-598.*
Wang, Jurfeng et al., "Study methods and application of image segmentation in medical image", Chin J. Med Imaging Technol, 2005, vol. 21 No. 10 pp. 1627-1630.

* cited by examiner

*Primary Examiner* — Jason M Repko
*Assistant Examiner* — Katrina Fujita
(74) *Attorney, Agent, or Firm* — Workman Nydegger

(57) ABSTRACT

The present invention discloses apparatus, method, and system for CT image processing; said apparatus comprises: an interface unit for obtaining CT images; a target region separation unit for separating said target region from the CT images by means of judging the CT values of voxel points in said CT images, wherein points with CT values greater than or equal to the threshold for target region separation constitute the target region, and said target region comprises at least one separate region; a false positive region removing unit for removing false positive regions from said target region and obtaining the accurate target region. The present invention can be used to quickly and conveniently determine the target region to be detected, measure the characteristic data of the target region, and display the physical and relative positions of the target region in a three-dimensional manner; with a lower threshold for target region separation, the present invention can reduce the omission rate of detection; in addition, on that base, the present invention can remove possible false positive regions, thereby describing the target region accurately and improve accuracy of target information.

19 Claims, 9 Drawing Sheets

1403　1401　　　　　　　1404　1402

APPARATUS, METHOD AND SYSTEM FOR COMPUTER TOMOGRAPHY IMAGE PROCESSING

FIELD OF THE INVENTION

The present invention relates to the field of image processing, particularly, to a method, apparatus and system for Computer Tomography image processing.

BACKGROUND OF THE INVENTION

Computer Tomography (CT) is a technique for scanning human body layers with X-rays under computer control. It utilizes the fact that different human tissues exhibit different densities under X-rays to perform comparison and thereby enabling the accurate display of an anatomical structure. Usually, the medical images obtained through CT are observed and analyzed by doctors or similar personnel so as to obtain pathological information, which is taken as the basis for diagnosis.

However, due to the fact that the number of tissues displayed in CT images is large and the boundaries between the tissues are blurring, only experienced doctors can obtain accurate pathological information from CT images. In addition, some pathological information may be neglected by the doctors, thereby causing incomplete information. For example, in the case of a CT scan of abdomen, a doctor obtains from the CT images certain pathological information with which calculi in the urinary system is thus analyzed, often resulting in misjudgments or incorrect judgments of calculi.

There was disclosed a prior art method for automatic generating color multi-windows CT images, which was for processing CT images so as to attain the purpose of highlighting pathological information and helping the doctor to obtain more and more accurate pathological information. The detailed description of that method is found in the patent application No. ZL200310118965.2. According to that method, CT images are separated into several regions such that different organs or tissues are assigned to different regions. The organs or tissues are assigned automatically based on the distribution ranges of the CT values of the organs or tissues in the CT images as well as the topological structure of the organs. Next, such regions are corrected. Then, such regions are colored with different colors. Finally, a pathological report is generated, and the multi-windows color CT image is printed out along with a diagnostic result.

However, the target regions cannot be highlighted accurately and directly in the CT images according to the prior art. As a result, the doctor cannot directly obtain some pathological information from the CT images, such as positions, attributes and other parameters of the target regions, and thus the doctor cannot obtain the complete image information.

In general, in the existing image processing techniques, especially CT image processing, it is an urgent technical task for those skilled in the art to enable the display of required target regions accurately from numerous, complicated, and similar image data.

SUMMARY OF THE INVENTION

The object of the present invention is to provide a CT image processing method and a CT image processing apparatus for determining target regions accurately, improving detection speed, and displaying physical and relative positions of target regions in a three-dimensional manner. Particularly, provided that the efficiency requirement is meet, characteristic data, such as, CT values, volumes, etc., can be accurately acquired through measurement of image points.

Another object of the present invention is to apply the above-described idea to actual clinical application environments, thereby providing a CT image processing system for determining various regions efficiently and accurately and displaying those regions on a display unit in a three-dimensional manner, so as to ensure that this method can be applied to the clinical applications.

To solve the above-mentioned technical problems, the present invention employs the following technical solution and provides a CT image processing apparatus, comprising:

An interface unit for obtaining CT images;

A target region separation unit for separating the target region from the CT images by judging CT values of voxel points in said CT images; wherein the points with CT values greater than or equal to the separation threshold constitute the target region; said target region comprises at least one separate region;

A false positive region removing unit for removing false positive regions in said target region and obtaining the accurate target region.

Preferably, said apparatus further comprises:

A detection region determination unit for determining the regions to be detected in the CT images in accordance with the detection demand; said target region separation unit separating the target region from the CT images by judging the CT values of voxel points in the regions to be detected in said CT images.

Preferably, said apparatus further comprises:

A volume rendering unit for determining the border points in the region to be enhanced in display in accordance with the gradients of the various points, and performing volume rendering for the region to be enhanced in display in accordance with the opacity values set for the border points and the non-border points;

A display unit for displaying said accurate target region and the region to be enhanced in display for comparison.

Wherein said false positive region removing unit may comprise: a tissue region separation component for separating specific tissue regions from said CT images; a removing component for removing the points in said specific tissue regions from the points in said target region;

Alternatively, said false positive region removing unit comprises: a gradient removing component for removing points with gradients less than or equal to the preset gradient threshold from the points in said target region;

Alternatively, said false positive region removing unit comprises: a region-of-interest determination component for determining a region of interest in said CT images in accordance with the detection demand; a position removing component for judging whether a certain separate region in said region of interest is completely or partially beyond said region of interest, and if so, removing all points constituting said separate region;

Alternatively, said false positive region removing unit comprises: a volume removing component for judging whether the volume of a certain separate region in said target region is greater than or equal to a preset volume threshold, and if so, removing all points constituting said separate region;

Alternatively, said false positive region removing unit comprises: a CT value distribution removing component for judging whether the standard deviation of CT values of a certain separate region in said target region is greater than or equal to the preset threshold, and if so, removing all points constituting said separate region.

Preferably, said apparatus further comprises: a characteristic data measuring unit for calculating characteristic data of separate regions in said accurate target region in accordance with the coordinates, voxel parameters, or CT values of the points in said accuracy target region.

In a preferred embodiment, said specific tissue region is a skeleton region, and said target is calculus. Said region to be enhanced in display is a kidney region, a ureter region, or a bladder region.

Wherein the method for separating said specific tissue regions is a region growing method; said tissue region separation component comprises: a seed point determination module for traversing all points in the slice nearest to the chest in said abdominal CT images, and taking the first one of the points with CT values greater than the preset separation threshold as the seed point; a region growing module for beginning region growing from said seed point, with points with CT values greater than or equal to the preset separation threshold constituting the specific tissue region. Preferably, said apparatus further comprises: a secondary seed point determination module for judging whether there is any point with CT value greater than said preset separation threshold but not assigned to said specific tissue region in the slice nearest to the chest in said abdominal CT images, and, if so, taking said point as the seed point and outputting the information to said region growing module.

The present invention also discloses a CT image processing method, comprising:

Obtaining CT Images;

Separating the target region from the CT images by judging CT values of voxel points in said CT images; wherein points with CT values greater than or equal to the target region separation threshold constitute the target region; said target region comprises at least one separate region;

Removing false positive regions from said target region to obtain the accurate target region.

Preferably, said method further comprises the following steps before the target region separation step: determining the region to be detected in said CT images in accordance with the detection demand; said target region separation unit separating the target region by judging the CT values of voxel points in said region to be detected in said CT images.

Furthermore, said method further comprises: determining the border points in the region to be enhanced in display in accordance with the gradients of the various points, setting different opacity values for border points and non-border points, and performing volume rendering for the region to be enhanced in display on said CT images in accordance with said opacity values; displaying said accurate target region and said region to be enhanced in display for comparison.

Wherein said false positive regions can be removed as follows:

Removing based on the tissue region: separate specific tissue regions from said CT images; remove the points in said specific tissue regions from the points in said target region;

Alternatively, removing based on the gradient: remove points with gradients less than or equal to the preset gradient threshold from the points in said target region;

Alternatively, removing based on the region of interest: determine the regions of interest in said CT images in accordance with the detection demand; judge whether a separate region in said target region is completely or partially beyond said region of interest, and if so, remove all points in said separate region;

Alternatively, removing based on the volume: judge whether the volume of a separate region in said target region is greater than or equal to the preset volume threshold, and, if so, remove all points in said separate region;

Alternatively, removing based on the CT value distribution: judge whether the standard deviation of CT values of a separate region in said target region is greater than or equal to the preset threshold, and, if so, remove all points in said separate region.

Preferably, said method further comprises: calculating the characteristic data of the enclosed separate regions in said accurate target region in accordance with the coordinates, voxel parameters, or CT values of the points in said accurate target region.

Wherein said method for separation of specific tissue regions is a region growing method, comprising: traversing the points in the slice nearest to the chest in said abdominal CT images, taking the first one of the points with CT values greater than the preset separation threshold as the seed point, and beginning region growing from said seed point, with points with CT values greater than or equal to the preset separation threshold constituting the specific tissue region. Preferably, said method further comprises: judging whether there is any point with CT value greater than said preset separation threshold but not assigned to said specific tissue region in the slice nearest to the chest in said abdominal CT images, and if so, taking said point as the seed point, and outputting the information to said region growing module.

The present invention also provides a CT image processing system, comprising:

An image scanning and reconstruction subsystem for using X-rays to scan the region to be detected and outputting the CT images;

An image processing subsystem for processing said CT images, comprising the following units:

An interface unit for obtaining CT images;

A target region separation unit for separating the target region from the CT images by judging CT values of voxel points in said CT images; wherein points with CT values greater than or equal to the separation threshold for a target region constitute the target region; said target region comprises at least one separate region;

A false positive region removing unit for removing false positive regions in said target region and obtaining the accurate target region;

A display subsystem for displaying said accurate target region.

Compared to the prior art, the present invention has the following advantages:

With image processing techniques, the present invention compares the CT values of the points in the CT images with the threshold of CT values to separate the target region, and then removes false positive regions from said target region; therefore, some target regions, especially regions with pathological changes, can be highlighted in the CT images quickly and conveniently.

The present invention employs a low threshold for target regions and thereby reducing the omission rate for the points in the target regions, so as to include all possible points in the target region; in addition, accordingly, the present invention employs all viable false positive region removing methods for the points in the target region, so as to include all possible false positive regions from said target region, thereby describing said target region accurately and improving the accuracy of information highlighting.

In addition, with image processing techniques, the present invention can determine the region to be detected in the CT images firstly in accordance with the detection demand, and can further determine the accurate target region only in the detected region, thereby improving the detection speed, effectively reducing errors, and improving the detection accuracy.

Furthermore, by calculating coordinates, voxel parameters, or CT values of the points in the accurate target region, the present invention further calculates the characteristic data of the enclosed separate regions in the accurate target region; since the accurate target region can be described accurately with the image points, the present invention can improve accuracy of the characteristic data.

Furthermore, the present invention determines the border points of the region to be displayed by means of the gradients of the points, and performs volume rendering in accordance with the opacity values set for border points and non-border points; therefore, the present invention can highlight the target region in the region to be enhanced in display, and display the physical and relative positions of the region in a three-dimensional manner, so as to avoid the occurring of the case that the information of the target region cannot be obtained because the target region is in a tissue region though it exists.

DETAILED DESCRIPTION OF THE EMBODIMENTS

To make above objects, features and advantage of the present invention understood more clearly and easily, hereunder the present invention will be further detailed in the embodiments with reference to the accompanying drawings.

Figure 1:
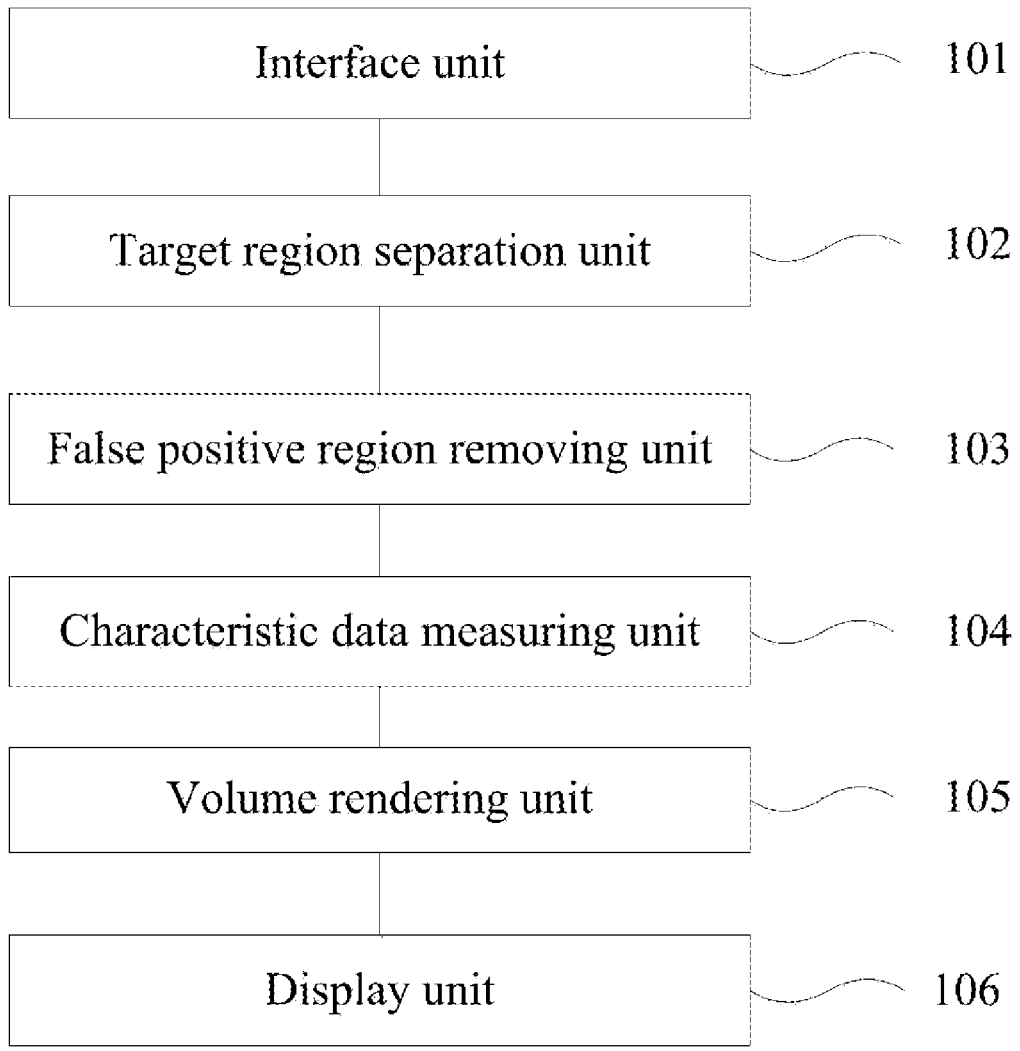
FIG. 1 is a structural block diagram of a CT image processing apparatus according to the present invention.

FIG. 1 shows a CT image processing apparatus according to the present invention; wherein said CT image processing apparatus comprises:

An interface unit 101 for obtaining CT images;

A target region separation unit 102 for separating the target region from the CT images by judging CT values of voxel points in said CT images; wherein points with CT values greater than or equal to the separation threshold for target region constitute the target region; said target region comprises at least one separate region;

A false positive region removing unit 103 for removing false positive regions in said target region and obtaining the accurate target region.

The interface unit 101 described in the present invention can obtain the CT images by a variety of ways, for example, obtain the CT images through a direct connection to the CT machine, through network data transmission, or via a mobile storage device, etc.

Figure 2:
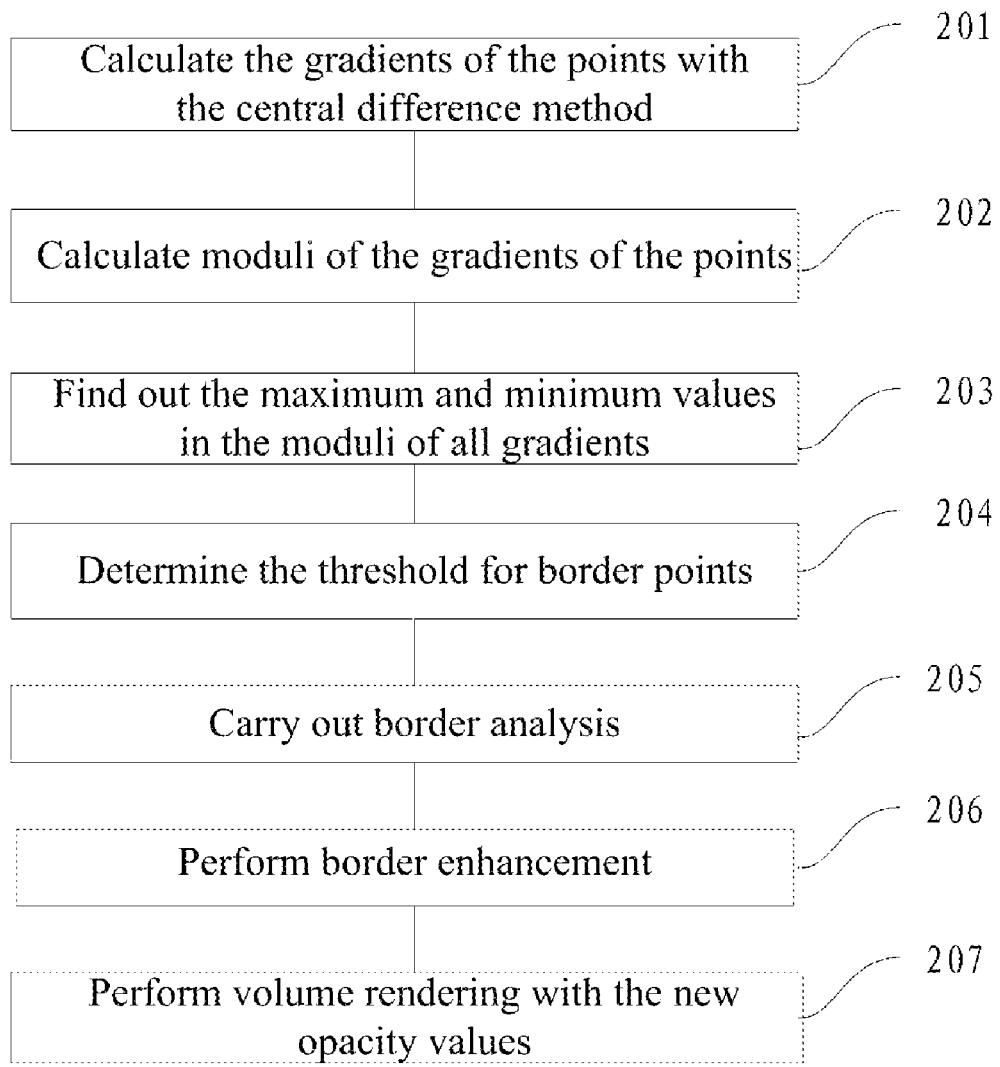
FIG. 2 is a flow diagram of border enhancement by the enhanced display unit in the apparatus shown in FIG. 1.

In order to effectively reduce detection time and improve detection accuracy significantly, a smaller region to be detected can be determined as required before the detection of the CT images obtained via interface unit 101, for example, the cardiac and pulmonary system, the alimentary system, or the urinary system; therefore, as shown in FIG. 2, the apparatus according to the present invention can further comprise a detection region determination unit for determining the region to be detected in said CT images in accordance with the detection demand, so that the target region separation unit 102 only needs to judge the CT values of the points in the region to be detected.

The region to be detected can be determined through the following steps: establish a Cartesian coordinate system for the three-dimensional data as follows: take any point as the origin, set the left hand direction of human body as the positive direction of X-axis, set the chest direction as the positive direction of Y-axis, and set the head direction as the positive direction of Z-axis; abstract a characteristic of the organ in the region to be detected, and project in all directions for the characteristic to obtain the projected curves of the characteristic in all directions; perform calculation and analysis for the projected curves to position the characteristic in the directions corresponding to the projected curves. The intersection set of the positioning results in the directions is the region to be detected. The determination procedures may vary depending on the specific detection demand. Hereunder the determination procedures are detailed in the example of determining the region to be detected in the urinary system. Of course, the region to be detected can also be determined in said CT images with any other method, for example, draw out the region to be detected manually with experience.

Attention should be paid to the setting of the threshold for target region separation. In order to improve the detection rate, the threshold should be set to a value less than or equal to the lower threshold Nc for CT values in the target region (in case that there are different lower thresholds Nc for CT values, the mean value of the lower thresholds Nc can be used, or a specific value can be used as required). Then, the CT values of the points in the region to be detected are compared with the threshold for region of interest separation, and the points with CT values greater than the threshold for target region separation are assigned to the target region. For example, in calculus detection, the calculus separation threshold can be determined as 100 in accordance with the clinical research result; then, any point with CT value greater than or equal to 100 is marked as a calculus point; the separate region constituted by all calculus points is determined as the target region.

In the implementations of the present invention, there are many factors that may cause errors of the target region, i.e., result in false positive regions; for example, the CT value ranges of some tissue regions in the CT images may overlap the CT value range of the target region, resulting in false positive regions in the target region; in such cases, the false positive regions must be removed.

To this end, the false positive region removing unit in the present invention may comprise: a tissue region separation component for separating specific tissue regions from said CT images; a removing component for removing the points of said specific tissue regions from the points of said region of interest. Wherein the separating method for said specific tissue region is a region growing method; said tissue region separation component comprises: a seed point determination module for traversing all points in the slice nearest to the chest in said abdominal CT images, and taking the first one of the points with CT values greater than the preset separation threshold as the seed point; a region growing module for beginning region growing from said seed point, with points with CT values greater than or equal to the preset separation threshold constituting the specific tissue region.

In order to further determine the specific tissue regions to be separated, said tissue region separation component may further comprise: a secondary seed point determination module for judging whether there is any point with CT value greater than said preset separation threshold but not assigned to a specific tissue region in the slice nearest to the chest in said abdominal CT images, and, if there is, take said point as the seed point and output the information to said region growing module.

Other factors that may cause false positive regions and the corresponding removing methods are detailed later in the description.

In order to provide more diagnostic information to medical personnel, especially, in order to obtain characteristic data (e.g., position, CT value, and volume, etc.) accurately by means of measurement of image points, as shown in FIG. 1, the apparatus according to the present invention can further comprise a characteristic data measuring unit 104, which is used for calculating characteristic data of the enclosed separate regions in said accurate target region in accordance with the coordinates, voxel parameters, or CT values of the points in said accurate target region. The algorithm of said characteristic data measuring unit 104 for the characteristic data is introduced as follows:

1. If a detected target region comprises n pixels with coordinates $(x_1, y_1, z_1), (x_2, y_2, z_2), \ldots (x_n, y_n, z_n)$, the position of the target (i.e., centroid (x, y, z)) can be calculated with the following expressions:

$$x = \frac{x_1 + x_2 + \ldots + x_n}{n}$$

$$y = \frac{y_1 + y_2 + \ldots + y_n}{n}$$

$$z = \frac{z_1 + z_2 + \ldots + z_n}{n}$$

2. Read the side lengths $X_{vox}$, $Y_{vox}$ and $Z_{vox}$ of data voxel from the CT data (Dicom format file); in view that the above target region comprises n pixels, the volume V of the target region is:

$$V = n \cdot X_{vox} \cdot Y_{vox} \cdot Z_{vox}$$

3. In view that the above target region comprises n pixels, the maximum, minimum, and mean CT values ($S_{max}$, $S_{min}$, $S_{mean}$) in the target region are:

$$S_{max} = \max(S_1, S_2, \ldots, S_n)$$

$$S_{min} = \min(S_1, S_2, \ldots, S_n)$$

$$S_{mean} = \frac{S_1 + S_2 + \ldots + S_n}{n}$$

In the present invention, since the calculation is made for all points included in the accurate target region in the CT images, more characteristic data can be calculated in accordance with the parameters of the points, not limited to the above position, volume, and CT value. In addition, the calculation in the present invention can be made with corrected expressions or expressions modified for other purposes; therefore, the calculation is not limited in the present invention. Those skilled in the art can choose the expressions as required.

In actual applications, the display of the obtained region is often not accurate enough yet, even though the above parameters are obtained; therefore, as shown in FIG. 1, the apparatus according to the present invention can further comprise a volume rendering unit 105 for displaying accurately the position of the accurate target region relative to the neighboring tissues; said volume rendering unit 105 is implemented as follows: determine the border points of the region to be enhanced in display in accordance with the gradients of the points, set different opacity values for border points and non-border points, and perform volume rendering for the region to be enhanced in display in said CT images in accordance with opacity values. Preferably, if said volume rendering unit 105 is used to display calculi accurately, said region to be enhanced in display is kidney region, ureter region, or bladder region.

Preferably, the present invention further comprises a display unit 106 for displaying the detection result, measuring result, or volume rendering result, so as to facilitate the doctor or relevant persons to observe. Said detection result refers to: display the obtained accurate target region in the CT images by means of dyed borderlines for the purpose of highlighting. Said measuring result refers to: display the characteristic data obtained through measurement of said accurate target region. In view that the detection result is 2D displayed and not intuitive enough, it is difficult for the medical personnel to find out the position of the accurate target region relative to the neighboring tissues intuitively. With the volume rendering unit 105, the display unit 106 can display the volume rendering result, so that the doctor or relevant persons can observe in a three-dimensional view.

FIG. 2 describes in detail the volume rendering by border enhancement; comprising the steps of:

Step 201: calculate the gradients of the points with the above central difference algorithm;

Step 202: calculate the modulus ‖Gradient‖ of the gradients of the points with the following algorithm:

$$\|Gradient\| = \sqrt{Gradient_x^2 + Gradient_y^2 + Gradient_z^2}$$

Step 203: Find out the maximum ‖$Gradient_{max}$‖ and minimum ‖$Gradient_{min}$‖ from the moduli of all gradients;

Step 204: determine the limits LimitValue for border points:

$$LimitValue=(\|Gradient_{max}\|-\|Gradient_{min}\|)*LimitCoefficient+\|Gradient_{min}\|$$

Wherein the limit factor LimitCoefficient for limit analysis is in the range of [0, 1]; the specific value can be determined as required.

Step 205: carry out border analysis:

Analyze the modulus of gradient of each point with the following expression, to judge whether the point is on the border.

$$Grad = \begin{cases} 0 : \|Gradient\| \leq LimitValue \\ 1 : \|Gradient\| > LimitValue \end{cases}$$

Wherein Grad is the border information of the point; if Grad=0, it indicates the point is not on the border; if Grad=1, it indicate the point is on the border.

Step 206: Perform border enhancement;

Take $Grad_i$ as border information of point $(x_i, y_i, z_i)$ and $\alpha_i$ as the opacity value of the point, the opacity value $\alpha_i'$ after border enhancement is: $\alpha_i'=Grad_i*\alpha_i$ Step 207: perform volume rendering with the new opacity values.

It is noted that the volume rendering technique is to control the transparency of the drawn object by setting an opacity value; the less the opacity value is, the better the transparency effect will be. Border enhancement refers to modify opacity value of the drawn object with the border information to enhance transparency effect while keep the outline information of the drawn object. In the present invention, the method for volume rendering is not limited; those skilled in the art can choose a method as appropriate. In the present invention, after the display is enhanced with the above method, the physical and relative positions of the target region and other regions can be displayed accurately.

Figure 3:
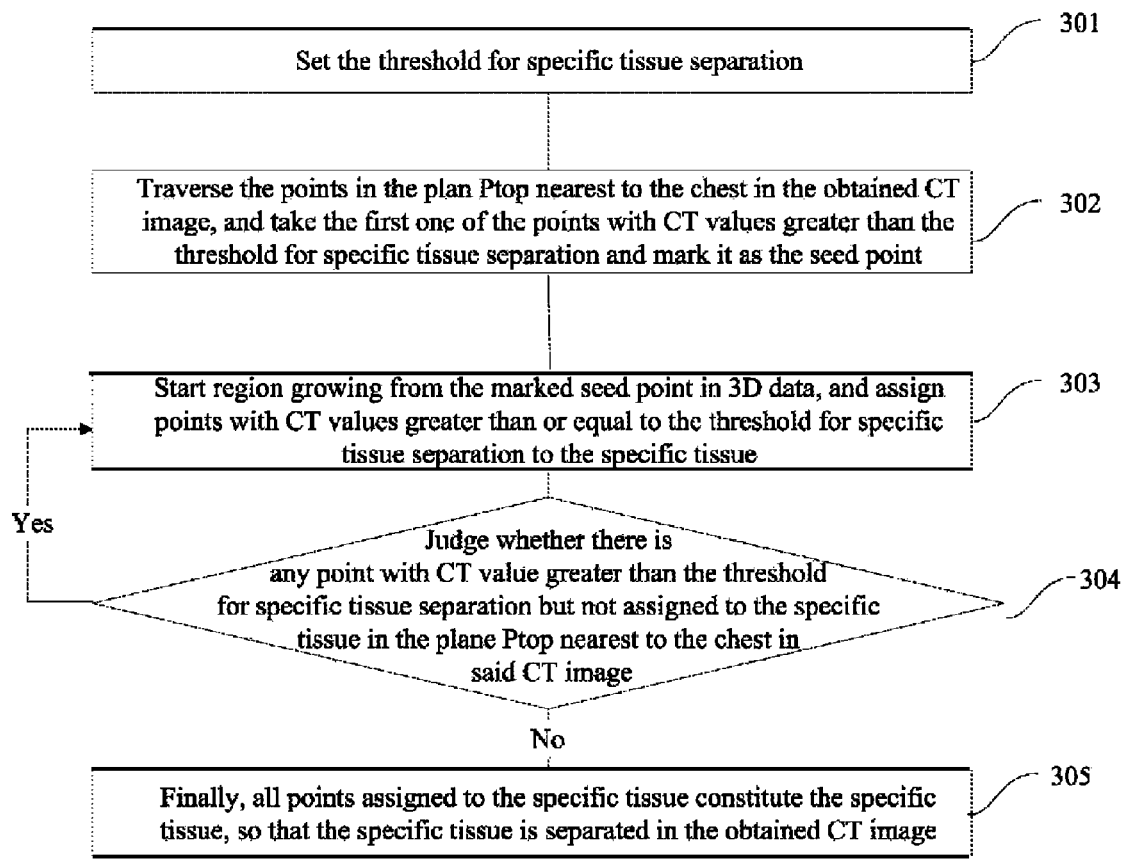
FIG. 3 is a flow diagram of separating a specific tissue region with a region growing method as described in the present invention.

FIG. 3 shows a flow diagram of separating specific tissue regions in the CT images with region growing method, comprising the steps of:

Step 301: set a separation threshold for specific tissue; said threshold can be chosen as required in accordance with the object to be detected;

Step 302: Traverse the points in the slice $P_{top}$ nearest to the chest in the obtained CT images, and take the first one of the points with CT values greater than the separation threshold for specific tissue as the seed point;

Step 303: begin region growing in the three-dimensional data, starting from the seed point, and assign points with CT values greater than or equal to the separation threshold for specific tissue to the tissue;

Step 304: judge whether there is an point with CT value greater than the separation threshold for specific tissue but not assigned to the tissue in the slice $P_{top}$ nearest to the chest in said CT images; if there is, take the point as the seed point, and repeat step 203 to perform region growing in the three-dimensional data; the number of repetitions is not limited;

Step 305: finally, all points assigned to the specific tissue constitute the tissue, so that the specific tissue is separated from the obtained CT images.

With the region growing method, specific tissues can be separated in the obtained CT images accurately; in addition, with growing repetitions, the error can be avoided.

Of course, specific tissues can also be separated with other methods, such as separation by histogram threshold, region splitting and merging method, MRF model, or KNN algorithm, etc.; the methods are not limited in the present invention.

Hereunder some cases of removing false positive regions will be described.

Case 1: if specific tissue regions may cause interference to the target region easily, for example, in the abdominal CT images, the skeleton regions often cause interference to detection of the calculus region, the specific tissue regions have to be separated, and then the points in the specific tissue regions obtained with the above method are removed from the points in the target region; the remaining points constitute the accurate target region.

With the method shown in FIG. 3, the false positive region removing unit may comprise: a tissue region separation component for separating specific tissue regions from said CT images; a removing component for removing the points in said specific tissue regions from the points in said target region. In that way, the false positive regions resulted from specific tissue regions are removed.

The specific tissue regions causing false positive effect are different, depending on the target region detection demand; for example, after stomach intestine imaging with barium meal, the stomach intestine tissue will cause interference to detection of the calculus region; therefore, the stomach intestine tissue has to be separated. Those skilled in the art should choose an appropriate separation method in accordance with the actual conditions of the specific tissue.

Case 2: in actual applications, false positive regions may be resulted from local CT value errors due to poor image quality; in such a case, it is found in the display that the contrast between false positive region and neighboring tissues is apparently lower than the contrast between the genuine target region and the neighboring tissues; it is common knowledge that the gradient is proportional to the grayscale difference between adjacent pixels; therefore, on region borders, the grayscale values of pixels vary significantly, and the gradient values are higher; in non-border regions in the image, the grayscale values of pixels vary mildly, and the gradient values are lower; in equal-grayscale regions in the image, the gradients are zero. Therefore, the solution is: obtain the gradient image from the original image; traverse the points assigned to the target region; if the gradient of a point is lower than a reference value (a preset empirical value), remove the separate region containing the point. To this end, said false positive region removing unit comprise a gradient removing component for removing points with gradients less than or equal to the preset gradient threshold from the points of said target region.

In the present invention, the gradients can be calculated with central difference method, i.e., the gradient {$Gradient_x$, Gradient$_y$, Gradient$_z$} of a point (x, y, z) in the target region can be calculated with the following expression:

$$\begin{cases} Gradient_x = (f(x+1, y, z) - f(x-1, y, z))/2 \\ Gradient_y = (f(x, y+1, z) - f(x, y-1, z))/2 \\ Gradient_z = (f(x, y, z+1) - f(x, y, z-1))/2 \end{cases}$$

Wherein {Gradient$_x$, Gradient$_y$, Gradient$_z$} is the gradient information of point (x, y, z), f(x, y, z) is the CT value of point (x, y, z), point (x+1, y, z) is the point next to point (x, y, z) in positive direction of x-axis, point (x−1, y, z) is the point next to point (x, y, z) in negative direction of x-axis; point (x, y+1, z) is the point next to point (x, y, z) in positive direction of y-axis, point (x, y−1, z) is the point next to point (x, y, z) in negative direction of y-axis; point (x, y, z+1) is the point next to point (x, y, z) in positive direction of z-axis, point (x, y, z−1) is the point next to point (x, y, z) in positive direction of z-axis.

After a gradient threshold (usually an empirical value) for the points in the target region has been set, the gradients of the points in the target region have been compared with the threshold, and the points with gradients less than or equal to the gradient threshold have been removed; the remaining points constitute the accurate target region. Of course, the gradient image can be obtained with any other method, such as sobel algorithm; there is no limitation for the method in the present invention. However, it is noted that corresponding reference values are required for different gradient calculation methods.

Case 3: in actual applications, false positive region may occur due to incorrect position of the target region in the CT images; in such a case, the false positive region removing unit described in the present invention can comprise:

A region-of-interest determination component for determining the regions of interest in said CT images in accordance with the detection demand; for example, in the detection of calculi in urinary system, the kidney region, ureter region, and bladder region can be determined as the regions of interest, and thereby calculus detection will only be carried out in those regions, so as to improve detection speed and reduce false positive regions;

A position removing component for judging whether there is any separate region completely or partially beyond said region of interest in said target region; if there is, all points in said separate region will be removed; for example, in the detection of calculi in urinary system, in the points that are marked as calculus point with the above method, if a separate region composed of calculus points is completely or partially beyond said kidney region, ureter region, or bladder region, all points in said separate region will be removed.

Of course, if the present invention comprises the detection region determination unit mentioned in the description of FIG. 1, no false positive scenario resulted from incorrect position will occur; therefore, the above region-of-interest determination component and position removing component are unnecessary; however, the false positive region removing unit can comprise other components to remove false positive regions resulted from other factors.

Case 4: in actual applications, false positive region may occur due to incorrect volume of the target region in the CT images; in such a case, the false positive region removing unit described in the present invention can comprise:

A volume removing component for judging whether there is any separate region with volume greater than or equal to the preset volume threshold in said target region, and, if there is, remove all points constituting said separate region; for example, in the detection of calculi in urinary system, if the calculus is in kidney, it is impossible that the volume of the calculus exceeds the volume of kidney. Clinical researches have shown: usually the volume of kidney doesn't exceed $V_{kid}$; in the points marked as calculus obtained with the above method, if the volume of a separate calculus region exceeds $V_{kid}$, all points constituting that region should be removed.

Case 5: in actual applications, false positive region may occur due to incorrect CT value distribution in the target region in the CT images; in such a case, the false positive region removing unit described in the present invention can comprise:

A CT value distribution removing component for judging whether there is any separate region with standard deviation of CT values greater than or equal to the preset threshold, and, if there is, remove all points constituting said separate region.

It is known in the field: for genuine calculi, the CT value distribution is even; therefore, separate regions with CT value greater than or equal to the preset threshold Nc but uneven CT value distribution should be removed as follows: calculate the standard deviation of CT values for separate regions in the points in the region of interest; Suppose a separate region comprises n points, the mean CT value $S_{mean}$ is:

$$S_{mean} = \frac{S_1 + S_2 + \ldots + S_n}{n}$$

Then, the standard deviation SD(s) is:

$$SD(s) = \sqrt{\frac{(S_1 - S_{mean})^2 + (S_2 - S_{mean})^2 + \ldots + (S_n - S_{mean})^2}{n}}$$

If the standard deviation of said separate region is greater than or equal to the preset threshold Nc, all points in said separate region should be removed.

Of course, the scenarios of false positive regions and the number of false positive regions may be different, depending on the chosen detection method and image quality; often the scenarios can't be classified further, and the false positive regions can't be removed completely; however, the existence of false positive regions has severe adverse effect to detection accuracy; therefore, false positive regions should be removed as far as possible. With the above method, the present invention can avoid the possibility of errors in the apparatus as far as possible. In order to remove false positive regions as far as possible, the false positive region removing unit described in the present invention can comprises all the above components related to false positive region removal or any combination of the components.

Figure 4:
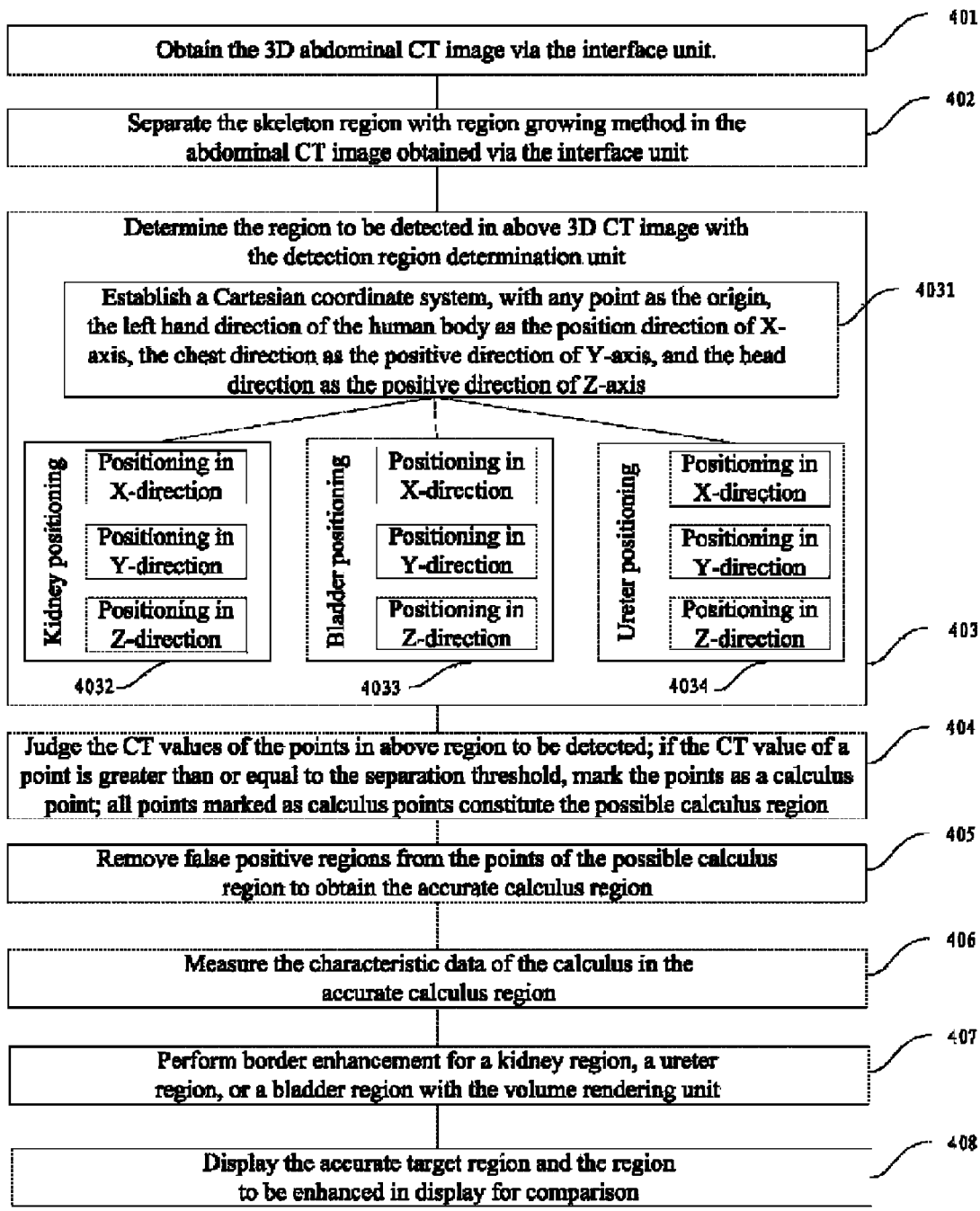
FIG. 4 is a flow diagram of image processing during the detection of calculi in the urinary system according to the present invention.
Figure 5:
FIG. 5 is a schematic diagram of a three-dimensional abdominal non-contrast CT images obtained in the embodiment shown in FIG. 4.

A preferred embodiment of the present invention is detection of calculi in urinary system; accordingly, the specific tissue region described in the present invention is skeleton region, and the target is calculus; said region to be enhanced in display is kidney region, ureter region, or bladder region. As shown in FIG. 4, when the apparatus according to the present invention is used for the detection, the present invention comprises the following steps:

Step 401: obtaining a 3D abdominal CT images, as shown in FIG. 5; wherein "a" in FIG. 5 is the coronal section view; "b" is the cross section view, and "c" is the sagittal section view.

Figure 6:
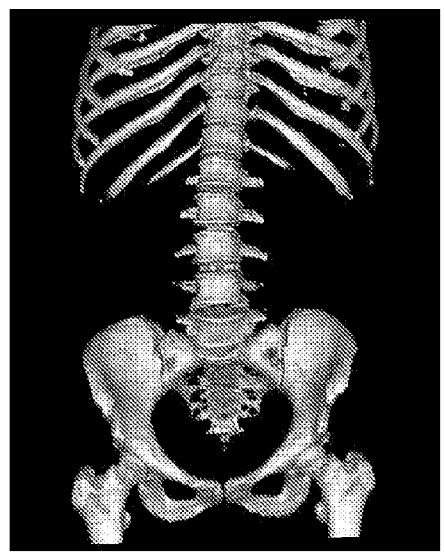
FIG. 6 is a schematic diagram of a skeleton region separated in the embodiment shown in FIG. 4.

Step 402: separating the skeleton region with a region growing method through the following steps in the abdominal CT images obtained via the interface unit:

Setting the threshold for skeleton region separation to 150;

Traversing the points in the slice $P_{top}$ nearest to the chest in the obtained abdominal CT images, and taking the first one of the points with CT values greater than the threshold for skeleton region separation (150) as the seed point;

Beginning region growing from the above seed point, and marking points with CT values greater than or equal to the threshold for skeleton region separation (150) as skeleton points; all points marked as skeleton points constitute the skeleton region;

Judging whether there is any point with CT value greater than 150 but not assigned to the skeleton region in the slice $P_{top}$ nearest to the chest in said abdominal CT images; if there is, taking that point as the seed point, and repeating the above step for region growing;

As shown in FIG. 6, finally, all points marked as skeleton points constitute the separate skeleton region.

Step 403: determining the region to be detected in the above 3D CT images with the detection region determination unit through the following steps:

Step 4031: establishing a Cartesian coordinate system as follows: take any point as the origin, set the left hand direction of human body as the positive direction of X-axis, set the chest direction as the positive direction of Y-axis, and set the head direction as the positive direction of Z-axis.

Step 4032: positioning the kidneys:

a. Positioning in X-Direction

Figure 7:
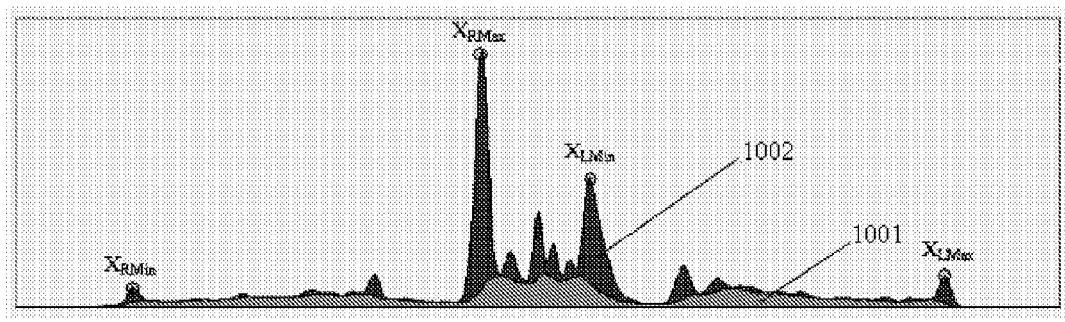
FIG. 7 is a schematic diagram of positioning curve and points in the X-direction for kidney positioning in the embodiment shown in FIG. 4.

As shown in FIG. 7, project the skeleton separation result in X-direction to obtain the project curve 1001; calculate the variance of each point on the projected curve 1001 on the neighboring region to obtain the variance distribution curve 1002; take the positions of 4 peaks at both ends and in the middle of the variance distribution curve 1002 as positioning points $X_{RMin}$, $X_{RMax}$, $X_{LMin}$, and $X_{LMax}$; wherein the region between point $X_{RMin}$ and point $X_{LMax}$ is the right kidney region, while the region between point $X_{LMin}$ and point $X_{LMax}$ is the left kidney region.

b. Positioning in Y-Direction

Figure 8:
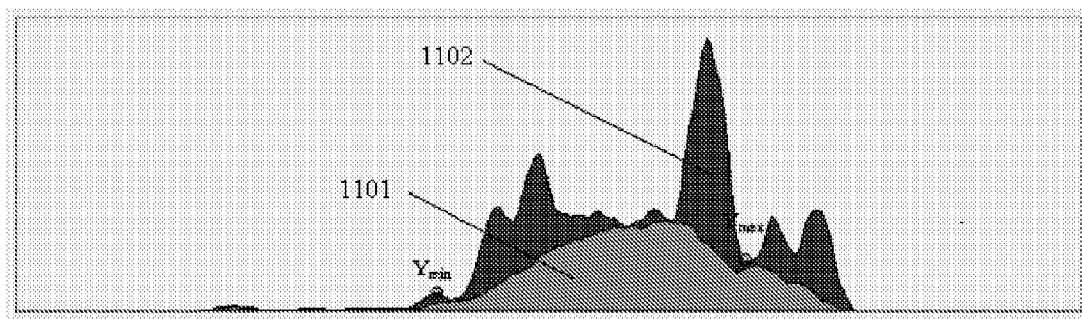
FIG. 8 is a schematic diagram of positioning curve and points in the Y-direction for kidney positioning in the embodiment shown in FIG. 4.

As shown in FIG. 8, project the skeleton separation result in Y-direction to obtain the projected curve 1101; calculate the variance of each point on the projected curve 1101 in the neighboring region to obtain the variance distribution curve 1102; take the wave valley after the maximum peak on the variance distribution curve 1102 as a positioning point $Y_{min}$; to obtain the other positioning point $Y_{max}$, work out the cumulative area sum curve in the negative direction, starting from point $Y_{min}$ on the projected curve on Y-axis at an increment N (N is an empirical value, taken as 10 in this embodiment); the position where the curve becomes mild is taken as the point $Y_{max}$. The region between positioning point $Y_{min}$ and $Y_{max}$ is the region of the kidneys.

c. Positioning in Z-Direction

Figure 9:
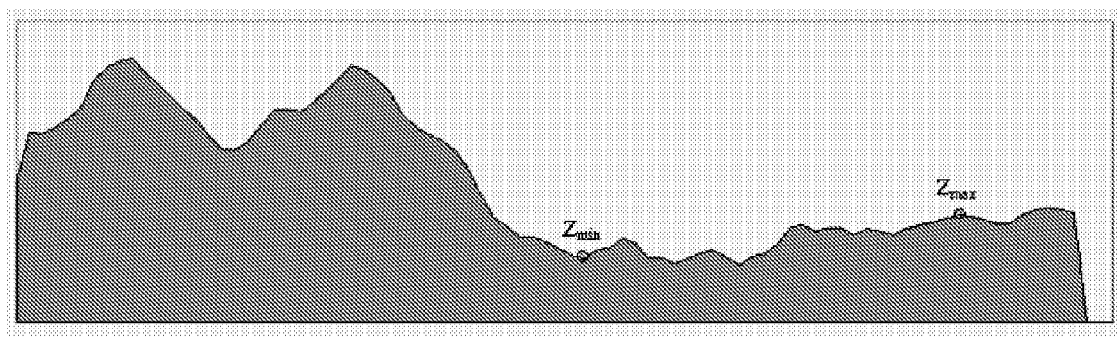
FIG. 9 is a schematic diagram of positioning curve and points in the Z-direction for kidney positioning in the embodiment shown in FIG. 4.

As shown in FIG. 9, project the skeleton separation result in Z-direction to obtain the projected curve; it is seen that there are apparently two peaks on the left of the curve, indicating denser skeleton distribution and thereby the projection result of pelvis; the distribution in the right portion of the curve is even, and the values are lower than those in the left portion, indicating the projection result of vertebra; take the joint between the two portions as a positioning point $Z_{min}$; calculate the other positioning point $Z_{max}$ in accordance with the physical length of kidney as well as data layer thickness, as follows: suppose the length of kidney is Lmm, the data layer thickness is Tmm, the length of kidney in the scan data is N=L/T layers, and $Z_{max}=N+Z_{min}$. The region between positioning point $Z_{min}$ and $Z_{max}$ is the region of kidneys.

Step 4033: positioning the bladders a. Positioning in X-Direction

Figure 10:
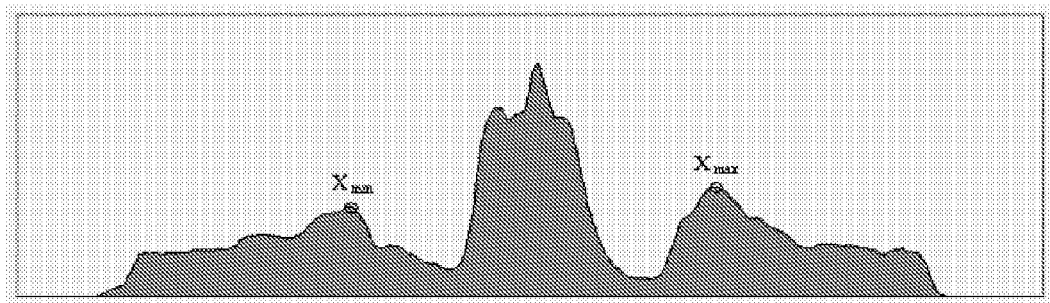
FIG. 10 is a schematic diagram of positioning curve and points in the X-direction for bladder positioning in the embodiment shown in FIG. 4.

As shown in FIG. 10, project the skeleton separation result in X-direction to obtain the projected curve; it is seen from the cross section view that the bladders are in the region between the femoral heads, corresponding to the region between point $X_{min}$ and $X_{max}$ on the projected curve.

b. Positioning in Y-Direction

Figure 11:
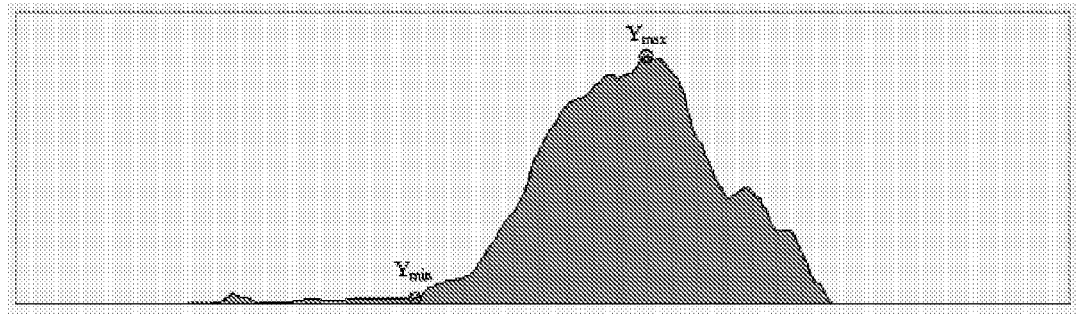
FIG. 11 is a schematic diagram of positioning curve and points in the Y-direction for bladder positioning in the embodiment shown in FIG. 4.

As shown in FIG. 11, project the skeleton separation result in Y-direction to obtain the projected curve; it is seen from the cross section view that the bladders are in the region between pubis and coccygeal vertebra, corresponding to the region between point $Y_{min}$ and $Y_{max}$ on the projected curve.

c. Positioning in Z-Direction

Figure 12:
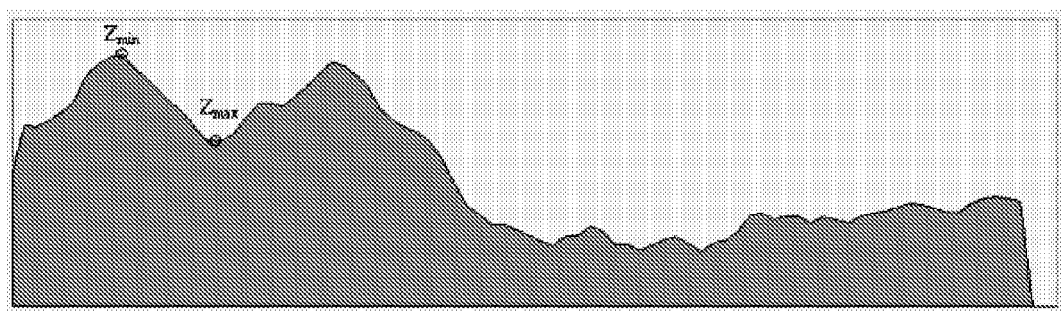
FIG. 12 is a schematic diagram of positioning curve and points in the Z-direction for bladder positioning in the embodiment shown in FIG. 4.

As shown in FIG. 12, project the skeleton separation result in Z-direction to obtain the projected curve; it is seen from the coronal section view that the bladders are in the region between femoral head and pubis, corresponding to the region between point $Z_{min}$ and $Z_{max}$ on the projected curve.

Step 4034: positioning ureters: with the above kidney and bladder positioning results, position in X, Y, and Z directions in the same way, to obtain the ureter region; the positioning method will not be described here further.

Figure 13:
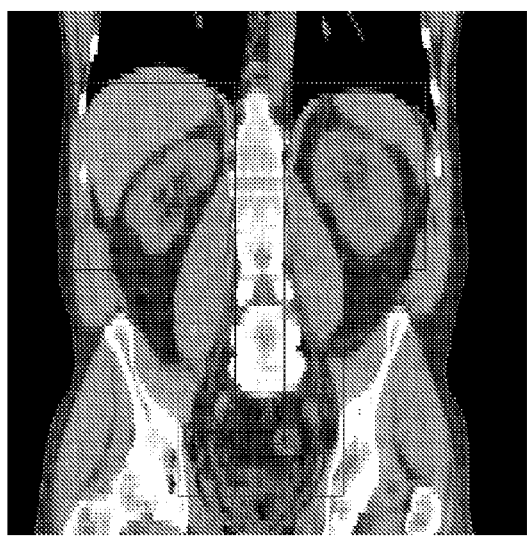
FIG. 13 is a schematic diagram of the determination result for the region to be detected in the urinary system in the embodiment shown in FIG. 4.

FIG. 13 shows the result of detection region determination in urinary system. Of course, determination of the region to be detected in urinary system is not a mandatory step; however, that step is helpful to reduce the detection time effectively and improve detection accuracy greatly. In addition, the above process and principle are also applicable to determine the regions of interest in the false positive region removing process.

Step 404: setting the threshold for calculus region separation to 100, and judging the CT value of each point in said region to be detected; if the CT value of a point is greater than or equal to 100, marking said point as a calculus point; all points marked as calculus points may constitute the calculus region.

Step 405: removing false positive regions from the points of the possible calculus region to obtain the accurate calculus region.

For example, the points in the skeleton region separated as described above can be removed from the points in the calculus region, so as to remove the false positive region with the CT value range of skeleton overlapping the CT value range of calculi and obtain the accurate calculus region. Of course, in other embodiments, the present invention can also employ the false positive region removing devices as described above to remove all possible false positive regions resulted from a variety of factors; the removing methods are as illustrated above and will not be detailed further here.

Step 406: measuring the characteristic data of calculi in the accurate calculus region with the algorithm as described above. The algorithm for characteristic data is as described above and will not be detailed further here. Hereunder a set of measured data is provided (see Table 1), to facilitate those skilled in the art to understand the foresaid calculation method.

TABLE 1

| No. | Position | Volume (mm³) | $CT_{max}$ | $CT_{min}$ | $CT_{mean}$ |
|---|---|---|---|---|---|
| 1 | (308, 265, 16) | 75.40 | 692 | 337 | 100 |
| 2 | (327, 252, 52) | 62.83 | 385 | 212 | 106 |
| 3 | (146, 298, 53) | 10.05 | 154 | 128 | 118 |
| 4 | (140, 296, 56) | 148.28 | 393 | 199 | 100 |

Step 407: performing border enhancement for the kidney region, ureter region, or bladder region with the volume rendering unit; the enhancement method is as described above and will not be detailed here. It is noted that the object to be rendered must be separated first before the volume rendering for border enhancement, i.e., the kidney region must be separated first. The method for kidney separation is not limited here, for example, it can be a region growing method, watershed method, or modeling method, etc.

Step 408: marking the accurate calculus region in the image with borderlines, and displaying the accurate calculus region on the display unit.

In this embodiment, the border enhancement technique is applied in kidney separation, and the enhancement result is displayed together with the calculus detection result; therefore, the size of calculus in kidney and the position of the calculus relative to kidney can be displayed accurately. The kidney region can be volume-rendered by means of border enhancement, while the calculus region can be displayed with ordinary borderlines; or, the opacity of the calculus region can be adjusted by volume rendering, so that the calculus region can be displayed more clearly by contrast, to provide clearer diagnostic information.

Figure 14:
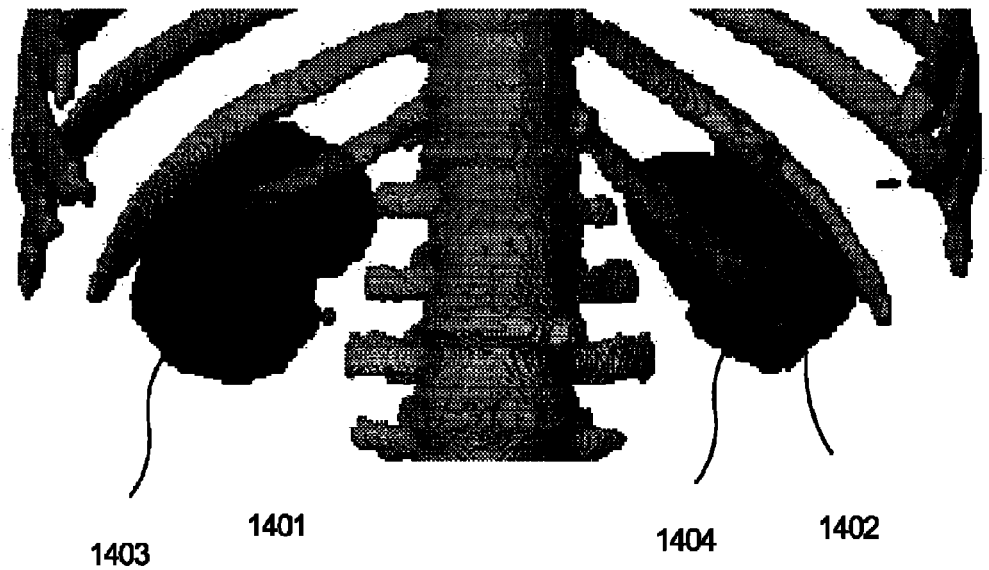
FIG. 14 is a schematic diagram of display of the detection result in the embodiment shown in FIG. 4.

The display result of the embodiment is shown in FIG. 14. As shown in FIG. 14, the two transparent regions evenly distributed along the skeleton are the volume-rendered regions (kidney regions) 1403 and 1404; they have been enhanced in transparency to highlight the calculus regions there; the separate region 1401 at bottom-right to the left volume-rendered region 1403 in FIG. 14 is a calculus region, and the separate region 1402 adjacent to the skeleton in the central part of the right volume-rendered region 1404 in FIG. 14 is also a calculus region.

In this step, relevant characteristic data obtained through measurement can also be displayed to be used by the medical personnel.

Figure 15:
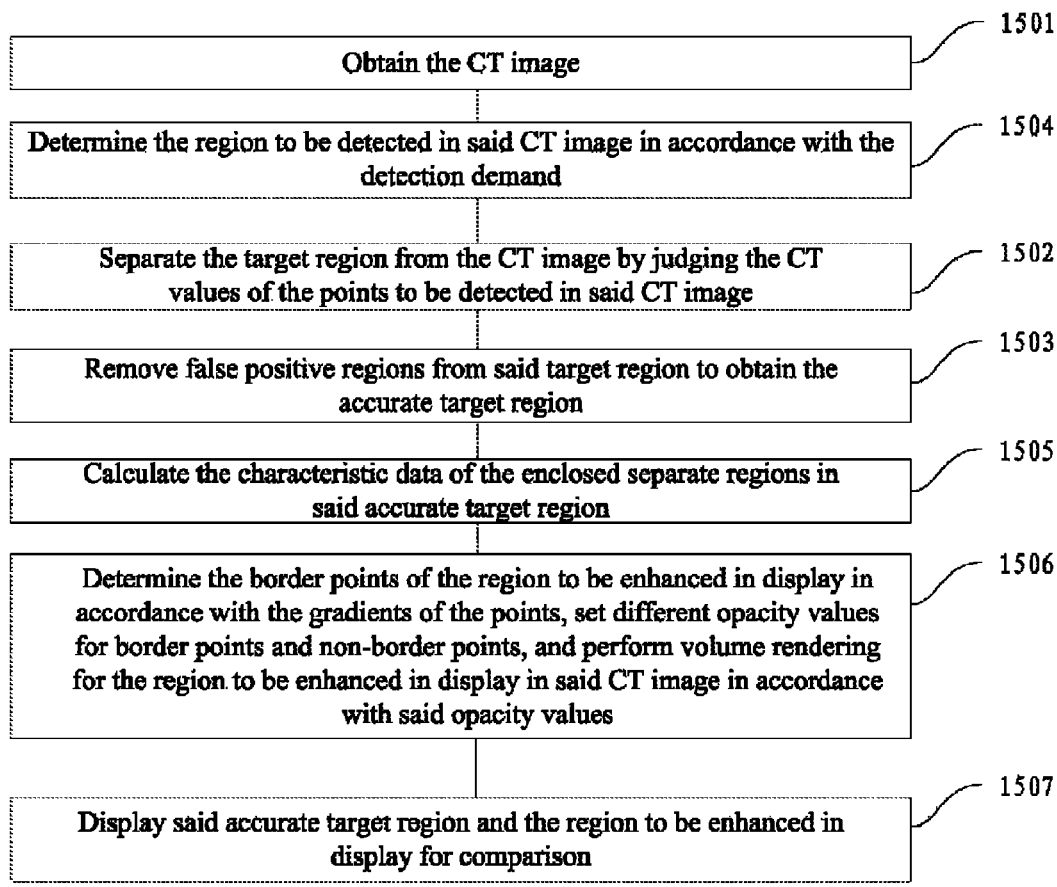
FIG. 15 is a flow diagram of the CT image processing method according to the present invention.

FIG. 15 shows the flow diagram of the CT image processing method according to the present invention; said method comprises the following steps:

Step 1501: obtaining CT images;

Step 1502: separating the target region from the CT images by judging CT values of voxel points in said CT images; wherein points with CT values greater than or equal to the threshold for target region separation constitute the target region; said target region comprises at least one separate region;

Step 1503: removing false positive regions from said target region to obtain the accurate target region.

Preferably, before the target region separation step, the method according to the present invention further comprises the following step 1504: determining the region to be detected in said CT images in accordance with the detection demand; said target region separation unit separating the target region from the CT images by judging the CT values of voxel points in said region to be detected in said CT images.

The present invention can provide a variety of false positive region removing approaches, including:

Removing based on the tissue region: separate specific tissue regions in said CT images; remove the points of said specific tissue regions from the points of said target region;

Alternatively, removing based on the gradient: remove points with gradients less than or equal to the preset gradient threshold from the points in said target region;

Alternatively, removing based on the region of interest: determine the region of interest in said CT images in accordance with the detection demand; judge whether a separate region in said target region is completely or partially beyond said region of interest, and if so, remove all points in said separate region;

Alternatively, removing based on the volume: judge whether the volume of a separate region in said target region is greater than or equal to the preset volume threshold, and, if so, remove all points in said separate region;

Alternatively, removing based on the CT value distribution: judge whether the standard deviation of CT values of a separate region in said target region is greater than or equal to the preset threshold, and, if so, remove all points in said separate region.

Preferably, said method further comprises step 1505: calculating the characteristic data of the enclosed separate regions in said accurate target region in accordance with the coordinates, voxel parameters, or CT values of the points in said accurate target region.

Furthermore, said method further comprises step 1506: determining the border points of the region to be enhanced in display in accordance with the gradients of the points, and setting different opacity values for border points and non-border points, and performing volume rendering for the region to be enhanced in display on said CT images in accordance with said opacity values; and step 1507: displaying said accurate target region and said region to be enhanced in display for comparison.

Preferably, said method for separation of specific tissue regions can a region growing method, comprising: traversing the points in the slice nearest to the chest in said abdominal CT images, taking the first one of the points with CT values greater than the preset separation threshold as the seed point, and beginning region growing, starting from said seed point, with points with CT values greater than or equal to the preset separation threshold constituting the specific tissue region. Preferably, said method further comprises the following step: judging whether there is any point with CT value greater than said preset separation threshold but not assigned to said specific tissue region in the slice nearest to the chest in said abdominal CT images, and if there is, taking said point as the seed point, and outputting the information to said region growing module.

Since the method shown in FIG. 15 can be implemented on the apparatus shown in FIG. 1 and the relevant content has been as detailed above, it will not be detailed further here.

Figure 16:
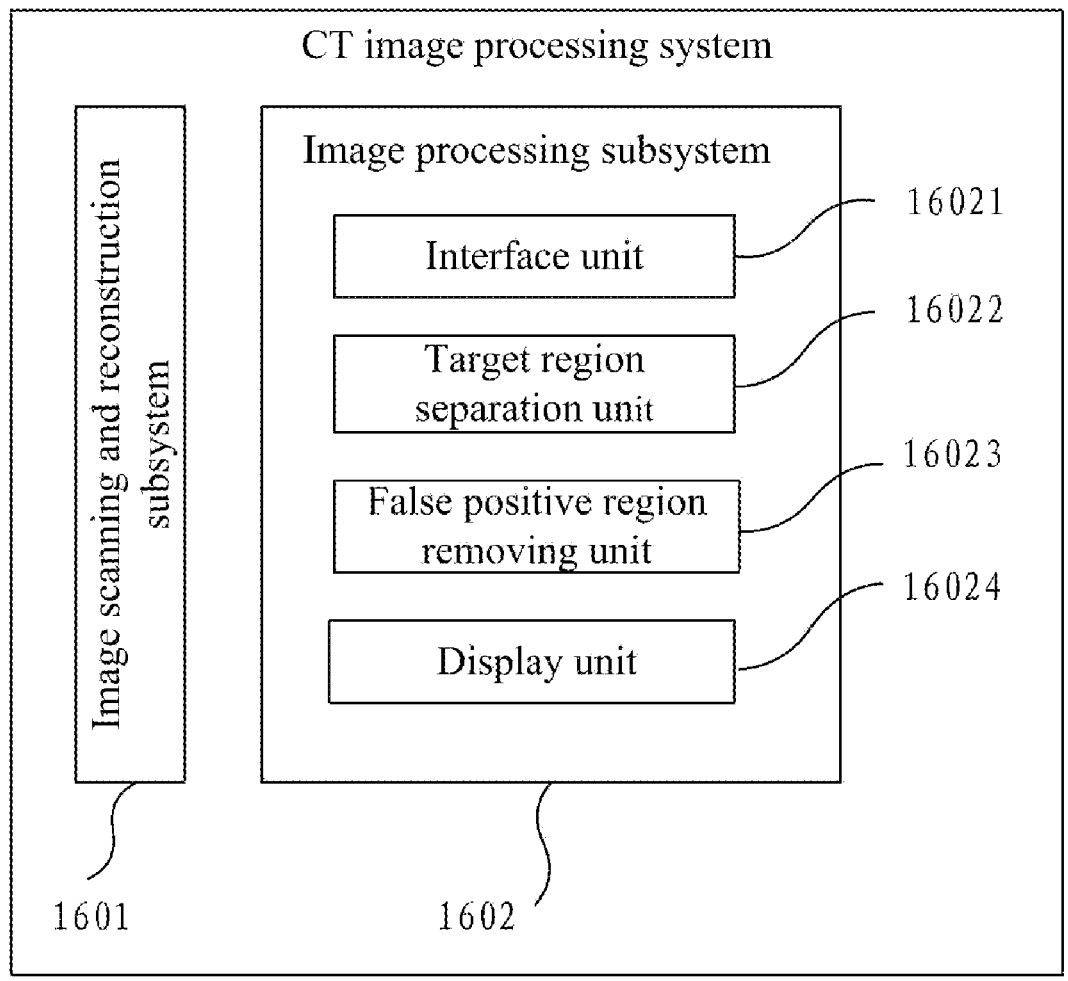
FIG. 16 is a structural block diagram of the CT image processing system according to the present invention.

With the core idea of the present invention, with reference to FIG. 16, a structural block diagram of the CT image processing system according to the present invention, the CT image processing system comprises the following components:

An image scanning and reconstruction subsystem 1601 for using X-rays to scan the region to be detected and output CT images;

An image processing subsystem 1602 for processing said CT images, comprising the following units:

An interface unit 16021 for obtaining CT images;

A target region separation unit 16022 for separating the target region from the CT images by judging CT values of voxel points in said CT images; wherein points with CT values greater than or equal to the threshold for target region separation constitute the target region; said target region comprises at least one separate region;

A false positive region removing unit 16023 for removing false positive regions from said target region and obtaining the accurate target region;

A display subsystem 16024 for displaying said accurate target region.

The image scanning and reconstruction subsystem can be implemented in any existing approach, and usually needs: an X-rays generator for generating X-rays, an X-ray detector for detecting X-rays transmitting through the sample under X-ray irradiation, and an image reconstruction unit for creating the image. Since that part is known to those skilled in the art, it will not be detailed here.

Of course, the system shown in FIG. 16 can further comprise the foresaid characteristic data measuring unit and volume rendering unit, etc.; See the above description for more information not shown in FIG. 16.

While the principle and implementation of the apparatus, method, and system for CT image processing according to the present invention has been illustrated and described with reference to some preferred embodiments, the embodiments are only used to facilitate understanding the technical solution and core idea of the present invention, and the present invention is not limited to them. Those skilled in the art should recognize that various variations and modifications can be made without departing from the spirit and scope of the present invention as defined by the accompanying claims.

What is claimed is:

1. A CT image processing apparatus, which is used to detect and display an accurate calculus region from three-dimensional abdominal non-contrast CT images, comprising:
   an interface unit for obtaining said three-dimensional abdominal non-contrast CT images;
   a detection region determination unit for determining automatically a kidney region, ureter region, or bladder region, which is used to limit a range of a calculus region, in said three-dimensional abdominal non-contrast CT images in accordance with a preset detection demand;
   a target region separation unit for separating the calculus region from the three-dimensional abdominal non-contrast CT images in the kidney region, ureter region, or bladder region;
   a false positive region removing unit for removing false positive regions from said calculus region and obtaining the accurate calculus region;
   wherein the detection region determination unit determines the kidney region, ureter region, or bladder region by the following manner:
   establishing a Cartesian coordinate system for the CT images as follows: taking any point as an origin, setting left hand direction of human body as a positive direction of X-axis, setting chest direction as a positive direction of Y-axis, and setting head direction as a positive direction of Z-axis;
   projecting skeleton separation result in X-axis, Y-axis and Z-axis to obtain all directions projected curves, calculating variance of each point within its neighborhood on the projected curves to obtain variance distribution curves, and determining the detection region by an analysis on characteristics of the variance distribution curves.

2. The apparatus as in claim 1, wherein said apparatus further comprises:
   a volume rendering unit for determining the border points of the region to be enhanced in display in accordance with the gradients of the points, and perform volume rendering for the region to be enhanced in display in said CT images in accordance with the opacity values set for border points and non-border points;
   a display unit for displaying said accurate target zone and the region to be enhanced in display for comparison.

3. The apparatus as in claim 2, wherein said region to be enhanced in display is a kidney region, ureter region, or bladder region.

4. The apparatus as in claim 1, wherein said false positive region removing unit comprises:
   a tissue region separation unit for separating specific tissue regions from said CT images;
   a removing component for removing the points in said specific tissue regions from the points in said target region.

5. The apparatus as in claim 4, wherein said specific tissue region is a skeleton region, and said target is calculus.

6. The apparatus as in claim 5, wherein said specific tissue region is separated with a region growing method; said tissue region separation component comprises:
   a seed point determination module for traversing the points in the slice nearest to the chest in abdominal CT images and take the first one of the points with CT values greater than the preset separation threshold as the seed point;
   a region growing module for starting region growing from said seed point, with points with CT values greater than or equal to the preset separation threshold constituting the specific tissue region.

7. The apparatus as in claim 6, wherein said tissue region separation component further comprises: a secondary seed point determination module, for judging whether there is any point with CT value greater than said preset separation threshold but not assigned to said specific tissue region in the slice nearest to the chest in said abdominal CT images, and, if there is, take that point as the seed point and output the information to said region growing module.

8. The apparatus as in claim 1, wherein said false positive region removing unit comprises:
   a gradient removing component for removing points with gradients less than or equal to the preset gradient threshold from the points in said target region.

9. The apparatus as in claim 1, wherein said false positive region removing unit comprises:
   a region-of-interest determination component for determining the regions of interest in said CT images in accordance with the detection demand;
   a position removing component for judging whether there is any separate region completely or partially beyond said region of interest in said target region; and, if there is, remove all points constituting said separate region.

10. The apparatus as in claim 1, wherein said false positive region removing unit comprises:
    a volume removing component for judging whether there is any separate region with volume greater than or equal to the preset volume threshold in said target region, and, if there is, remove all points constituting said separate region.

11. The apparatus as in claim 1, wherein said false positive region removing unit comprises:
    a CT value distribution removing component for judging whether there is any separate region with standard deviation of CT values greater than or equal to the preset threshold, and, if there is, remove all points constituting said separate region.

12. The apparatus as in claim 1, wherein said apparatus further comprises:
    A characteristic data measuring unit for calculating the characteristic data of the separate regions in the accurate target region in accordance with the coordinates, voxel parameters, or CT values of the points in said accurate target region.

13. A CT image processing method, which is used to detect and display an accurate calculus region from three-dimensional abdominal non-contrast CT images, comprising:
- obtaining said three-dimensional abdominal non-contrast CT images;
- determining automatically a kidney region, ureter region, or bladder region which is used to limit a range of a calculus region, in said three-dimensional abdominal non-contrast CT images in accordance with a preset detection demand;
- separating the calculus region from the three-dimensional abdominal non-contrast CT images in the kidney region, ureter region, or bladder region;
- removing false positive regions from said calculus region to obtain the accurate calculus region;
- wherein the step of determining the kidney region, ureter region, or bladder region comprises:
- establishing a Cartesian coordinate system for the CT images as follow: taking any point as an origin, setting left hand direction of human body as a positive direction of X-axis, setting chest direction as a positive direction of Y-axis, and setting head direction as a positive direction of Z-axis;
- projecting skeleton separation result in X-axis, Y-axis and Z-axis to obtain all directions projected curves, calculating variance of each point within its neighborhood on the projected curves to obtain variance distribution curves, and determining the detection region by an analysis on characteristics of the variance distribution curves.

14. The method as in claim 13, wherein said method further comprises:
- determining the border points of the region to be enhanced in display in accordance with the gradients of the points, and performing volume rendering for the region to be enhanced in display in said CT images in accordance with the opacity values set for border points and non-border points;
- displaying said accurate target region and the region to be enhanced in display for comparison.

15. The method as in claim 13, wherein said false positive region is removed through the following approach:
- removing based on the tissue region: separate specific tissue regions in said CT images;
- remove the points of said specific tissue regions from the points of said target region;
- alternatively, removing base on the gradient: remove points with gradients less than or equal to the preset gradient threshold from the points in said target region;
- alternatively, removing based on the region of interest: determine the region of interest in said CT images in accordance with the detection demand; judge whether a separate region in said target region is completely or partially beyond said region of interest, and if so, remove all points in said separate region;
- alternatively, removing based on the volume: judge whether the volume of a separate region in said target region is greater than or equal to the preset volume threshold, and, if so, remove all points in said separate region;
- alternatively, removing based on the CT value distribution: judge whether the standard deviation of CT values of a separate region in said target region is greater than or equal to the preset threshold, and, if so, remove all points in said separate region.

16. The method as in claim 15, wherein said specific tissue region separation method is a region growing method, comprising:
- traversing the points in the slice nearest to the chest in abdominal CT images, and taking the first one of the points with CT values greater than the preset separation threshold as the seed point;
- starting region growing from said seed point, with points with CT values greater than or equal to the preset separation threshold constituting the specific tissue region.

17. The method as in claim 16, wherein said method further comprises:
- judging whether there is any point with CT value greater than said preset separation threshold but not assigned to said specific tissue region in the slice nearest to the chest in said abdomen CT images, and if there is, taking said point as the seed point, and outputting the information to said region growing module.

18. The method as in claim 13, wherein said method further comprises:
- calculating the characteristic data of the enclosed separate regions in said accurate target region in accordance with the coordinates, voxel parameters, or CT values of the points in said accurate target region.

19. A CT image processing system, comprising:
- an image scanning and reconstruction subsystem for using X-rays to scan a region to be detected and output CT images;
- an image processing subsystem for processing said CT images, which is used to detect and display an accurate calculus region from three-dimensional abdominal non-contrast CT images, comprising the following units:
- an interface unit for obtaining said three-dimensional abdominal non-contrast CT images;
- a detection region determination unit for determining automatically a kidney region, ureter region, or bladder region, which is used to limit a range of a calculus region automatically in said three-dimensional abdominal non-contrast CT images in accordance with a preset detection demand;
- a target region separation unit for separating the calculus region from the three-dimensional abdominal non-contrast CT images in the kidney region, ureter region, or bladder region;
- a false positive region removing unit for removing false positive regions from said calculus region and obtaining the accurate calculus region;
- a display subsystem for displaying said accurate target region wherein the detection region determination unit determines the kidney region, ureter region, or bladder region by the following manner:
- establishing a Cartesian coordinate system for the CT images as follows: taking any point as an origin, setting left hand direction of human body as a positive direction of X-axis, setting chest direction as a positive direction of Y-axis, and setting head direction as a positive direction of Z-axis;
- projecting skeleton separation result in X-axis, Y-axis and Z-axis to obtain all directions projected curves, calculating variance of each point within its neighborhood on the projected curves to obtain variance distribution curves, and determining the detection region.

* * * * *